US005770357A

United States Patent [19]
Douvas et al.

[11] Patent Number: 5,770,357
[45] Date of Patent: Jun. 23, 1998

[54] METHOD OF DIAGNOSING CAPRINE ARTHRITIS-ENCEPHALITIS VIRUS INFECTION

[76] Inventors: Angeline Douvas, 345 S. Grand Oaks Ave., Pasadena, Calif. 91107; Glenn Ehresmann, 1941 Meadowbrook Rd., Altadena, Calif. 91101

[21] Appl. No.: 616,855

[22] Filed: Mar. 15, 1996

[51] Int. Cl.⁶ .............................. C12Q 1/70; G01N 33/53; G01N 33/544; G01N 33/536

[52] U.S. Cl. .............................. 435/5; 435/792; 435/793; 435/971; 436/528; 436/536; 436/543; 530/324; 530/325; 530/326; 530/327; 530/328; 530/329; 530/330

[58] Field of Search .............................. 435/5, 7.92, 7.93, 435/971; 436/528, 536, 543; 530/324, 325, 326, 327, 328, 329, 330

[56] References Cited

U.S. PATENT DOCUMENTS 5,462,852  10/1995  Arthur et al. .............................. 435/5

OTHER PUBLICATIONS

Lichtensteiger, et al.: Recombinant gp135 glycoprotein of Caprine Arthritis–Encephalitis Lentivirus Variants . . . : Virology: 185: pp. 2–9, 1991.

Voller, et al.: Enzyme immunoassays in diagnostic medicine: Bull. World Health Organ.: 53:pp. 55–65, 1976.

Rosati, et al.: Genetic and antigenic characterization of CAEV . . . : Vet. Microb.: 45: pp. 363–370, 1995.

Serruya, et al. : Identification of novel CAEV . . . : AIDS Res. and Hum. Retro: vol. 10, S1: PS54, 1994.

Cheevers et al., "Caprine arthritis–encephalitis lentivirus (CAEV) challenge of goats immunized with recombinant vaccinia virus expressing CAEV surface and transmembrane envelope glycoproteins", *Veterinary Immunology And Immunopathology* 4:3–4 (1994).

Knowles et al., "*Structure and Genetic Variability of the Envelope Glycoproteins of Two Antigenic Variants of Caprine Arthritis–Encephalitis Lentivirus*", J. of Virology 65:11 (1991).

Serruya and Gelman, "Identification of novel CAEV–like Lentivrus pol sequences and CAEV–antigen reactivity in HIV–associated Kaposi's sarcoma lesions," *AIDS Research and Human Retroviruses*, V10, S1 (Aug.) PS54 (1994).

Douvas, Angeline S., "Autoantibodies Occuring in Two Different Rheumatic Diseases React with the Same Nuclear Ribonucleoprotein Particle." *Proc. Natl. Acad. Sci. USA* 79:5401–5405 (1982).

Douvas, Angeline and Takehana, Yoshi Cross–Reactivity Between Autoimmune Anti–U1 snRNP Antibodies and Neutralizing Epitopes of HIV–1 gp120/41. *Aids Research and Human Retroviruses* 10:253–262 (1994).

*Primary Examiner*—Lynette F. Smith
*Assistant Examiner*—Brett Nelson
*Attorney, Agent, or Firm*—McCutchen, Doyle, Brown & Enersen

[57] ABSTRACT

The present invention provides a method of diagnosing caprine arthritis-encephalitis virus infection (CAEV) in a human sample suspected of being infected with CAEV.

6 Claims, No Drawings

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Glu Arg Lys Arg Glu Gly Phe Thr Ala Gly
1               5                   10

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Ser His His Gly Asn Asp Ser Arg Arg Arg
1               5                   10

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Ser Arg Arg Arg Arg Arg Lys Ser
1               5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Arg Lys Glu Thr Gly Thr Leu Gly Gly
1               5

( 2 ) INFORMATION FOR SEQ ID NO:5:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Arg Lys Lys Arg Glu Leu Ser His Lys Arg Lys Lys Arg
1               5                   10

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Arg Met Gln Arg Lys Glu Arg His Lys
1               5

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Val  Arg  Ser  Ser  Tyr  Gly  Ile  Thr  Ser  Ala
1                   5                        10
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Gly  Arg  Ile  Lys  Leu  Gln  Gly  Ile  Gly  Gly
1                   5                        10
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Gln  Glu  Ile  Leu  Glu  Asp  Trp  Ile  Gln  Gln
1                   5                        10
```

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Lys  Arg  Ile  Asn  Asn  Lys  Tyr  Asn  Lys  Asn  Ser
1                   5                        10
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Asp  Gly  Leu  Leu  Glu  Gln  Glu  Glu  Lys  Lys
1                   5                        10
```

( 2 ) INFORMATION FOR SEQ ID NO:12:

( i ) SEQUENCE CHARACTERISTICS:
        ( A ) LENGTH: 10 amino acids ( B ) TYPE: amino acid
        ( D ) TOPOLOGY: linear ( i i ) MOLECULE TYPE: peptide ( x i ) SEQUENCE DESCRIPTION: SEQ ID NO:12:

Ser Val Phe Pro Ile Val Val Gln Ala Ala
1               5                   10

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Ala Ile Asp Ala Glu Pro Thr Val
1               5

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GCAGTTGGCA TATTATGCTA CTAC                                                                  24

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CTTGTTGTAC TCTTTGTCCT AGTG                                                                  24

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GAGCAGTAAG ACATATGGCG GCAC                                                                  24

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TGATGCATTT GTATATAAGA TAGTGTTAGC TT                                                          32

( 2 ) INFORMATION FOR SEQ ID NO:18:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:18:

GGATTTGAAC TACACCCGCA G                        21

( 2 ) INFORMATION FOR SEQ ID NO:19:

( i ) SEQUENCE CHARACTERISTICS:
                    ( A ) LENGTH: 25 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:19:

CCTGTTGATA CTATGAACCC TAGAC                    25

( 2 ) INFORMATION FOR SEQ ID NO:20:

( i ) SEQUENCE CHARACTERISTICS:
                    ( A ) LENGTH: 22 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:20:

AAGAACCTAA GCATCCCGCA AC                       22

( 2 ) INFORMATION FOR SEQ ID NO:21:

( i ) SEQUENCE CHARACTERISTICS:
                    ( A ) LENGTH: 28 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:21:

GTGATGTTCC CTAATTGCAA TTCTAGTC                 28

METHOD OF DIAGNOSING CAPRINE ARTHRITIS-ENCEPHALITIS VIRUS INFECTION

This work was supported, in part, by grant 5-UO1-HD32632 awarded by the National Institutes of Health. The United States Government has certain rights in this invention.

BACKGROUND OF THE INVENTION

1. Field of the Invention

This invention relates generally to the fields of immunology and medicine and more specifically to a method of diagnosing caprine arthritis-encephalitis virus infection in an individual.

2. Background Information

Caprine arthritis-encephalitis virus (CAEV) is a retrovirus that is closely related to the human immunodeficiency virus (HIV-1), which causes AIDS in humans. CAEV is known to infect goats, where it causes various pathologic conditions, including arthritis and encephalitis. CAEV infection occurs world wide and can result in costly losses to the goat farming industry.

In many parts of the world, goat milk commonly is consumed and, particularly, in less developed countries, is an important source of nutrition. However, goat milk seldom is pasteurized in such countries prior to human consumption. Also, the consumption of raw goat milk is increasing in the United States due to its availability in health food markets. It now has been recognized that CAEV can infect humans, particularly those individuals who are occupationally exposed to goats or consume raw goat milk. While it has not yet been determined whether CAEV can cause a pathologic condition in humans, the close relationship of CAEV and HIV-1 suggests that it would be best to minimize the occurrence of CAEV infection in humans.

The simplest method to prevent CAEV infection of humans is to identify and isolate CAEV infected goats, thus preventing spread of the virus to humans as well as to other goats. Such a method of diagnosing CAEV infection also would be useful for identifying CAEV infected humans and for identifying CAEV infected blood supplies and can provide a means to determine whether CAEV infection in humans is associated with a pathologic condition. In particular, it is important to have a method of detecting CAEV infection in the blood supply because a syndrome associated with CAEV infection may occur only in a very young child receiving infected blood through a transfusion. Unfortunately, no convenient method is available for identifying the presence of a CAEV infection. Thus, a need exists for a simple and inexpensive method for diagnosing the presence of CAEV infection. The present invention satisfies this need and provides additional advantages.

SUMMARY OF THE INVENTION

The present invention provides a method of diagnosing caprine arthritis-encephalitis virus (CAEV) infection in a sample suspected of being infected with CAEV. For example, the invention provides an enzyme linked immunoadsorption assay (ELISA), wherein CAEV gp135 is bound to a solid support and wherein, upon contacting the CAEV gp135 with a sample such as a serum sample obtained from an individual suspected of being infected with CAEV, the detection of an antibody in the serum that binds to CAEV gp135 is diagnostic of CAEV infection in the individual. The invention also provides a kit for performing such an ELISA.

DETAILED DESCRIPTION OF THE INVENTION

The present invention provides method of diagnosing a caprine arthritis-encephalitis virus (CAEV) infection in a sample suspected of being infected with CAEV. Based on the studies disclosed herein, a significant population of persons, particularly in Mexico and Central America, may be infected with CAEV. The present invention provides a simple and inexpensive method for diagnosing an individual infected with CAEV.

A method of the invention is exemplified by an enzyme linked immunoadsorption assay (ELISA), which can be used to diagnose the presence of a CAEV infection in an individual suspected of having a CAEV infection. Such an ELISA is performed by obtaining a sample such as a blood sample from the individual, contacting the sample with a CAEV antigen and detecting binding of an anti-CAEV antibody present in the sample to the CAEV antigen, wherein such a detection is diagnostic of CAEV infection.

As used herein, the term "sample," when used in reference to a diagnostic method of the invention, means a tissue specimen or a fluid specimen such as a blood, which can be whole blood, plasma or serum, or a urine specimen, which is obtained from an individual such as a human, goat or other mammal to be tested for CAEV infection. Methods of obtaining such a sample, including an appropriate tissue sample, are well known and routine in the art.

As used herein, the term "CAEV antigen" means a CAEV viral particle or a portion of a CAEV viral particle, which can be a portion of a CAEV viral particle or a peptide fragment of a CAEV protein such as a peptide fragment of the gp135 envelope glycoprotein, that is recognized by and can be bound by an anti-CAEV antibody (see Table 1; env). CAEV is readily available from the American Type Culture Collection (ATCC VR-905).

A CAEV antigen is characterized in that it can stimulate an immune response, either in vivo or ex vivo and, therefore, can be used as a ligand for binding an anti-CAEV antibody in a method of the invention. For example, the ELISA disclosed in Example I.C. utilizes CAEV gp135 as the CAEV antigen. However, a CAEV antigen useful in a method of the invention can be selected from essentially any antigenic fragment of CAEV or can be the entire CAEV viral particle.

A CAEV antigen can stimulate an immune response against CAEV when administered to a human, a goat or other mammal and, therefore, can generate the production of anti-CAEV antigen antibodies in the individual. The presence of such antibodies in an individual are diagnostic of CAEV infection in the individual.

Prior to the present disclosure, it was not known that CAEV can infect humans. As disclosed herein, however, CAEV infection of human may be prevalent, particularly in populations where consumption of raw goat milk is common or where individuals in a population are otherwise exposed to goats (see Example I.C.). While it has not yet been determined whether CAEV infection causes a pathology such as arthritis or encephalitis in humans as it does in goats, if such a CAEV induced pathology

TABLE 1

CAEV ANTIGENS

| | | | |
|---|---|---|---|
| env | 26 | ERKREGFTAG | (SEQ ID NO: 1) |
| | 48 | SHHGNDSRRR | (SEQ ID NO: 2) |
| | 54 | SRRRRRKS | (SEQ ID NO: 3) |
| | 514 | RKETGTLGG | (SEQ ID NO: 4) |
| | 620 | RKKRELSHKRKKR | (SEQ ID NO: 5) |
| pol | 13 | RMQRKERHK | (SEQ ID NO: 6) |
| | 37 | VRSSYGITSA | (SEQ ID NO: 7) |
| | 83 | GRIKLQGIGG | (SEQ ID NO: 8) |
| | 307 | QEILEDWIQQ | (SEQ ID NO: 9) |
| | 1033 | KRINNKYNKNS | (SEQ ID NO: 10) |
| gag | 123 | DGLLEQEEKK | (SEQ ID NO: 11) |
| | 141 | SVFPIVVQAA | (SEQ ID NO: 12) |
| | 306 | AIDAEPTV | (SEQ ID NO: 13) | env, pol and gag refer to the envelope, polymerase and nucleocapsid core protein coding regions, respectively, of CAEV. Numbers preceding each sequence indicates the amino acid position in each CAEV protein that corresponds to the first amino acid shown for each peptide.

exists, then it will be important to vaccinate persons involved in the goat farming industry against CAEV infection.

A diagnostic method of the invention such as the ELISA assay exemplified herein can be useful to identify CAEV infected individuals. Such a method of the invention also can be particularly useful, for example, to screen blood supplies to identify CAEV infected blood, thereby preventing the spread of CAEV infection through administration of CAEV contaminated blood. In addition, in some cases it can be desirable to administer a vaccine comprising a CAEV antigen to an individual. In such a case, a diagnostic method of the invention can be useful to follow the generation of an immune response against CAEV in such a vaccinated individual. Furthermore, since it has now been determined that CAEV infects humans, it is recognized that there is a likelihood that CAEV also can infect other mammals, including, for example, cows, horses, sheep, dogs, cats or other mammals. Thus, an ELISA of the invention can be useful for diagnosing CAEV infection in any such mammal.

Methods and reagents for performing a diagnostic assay of the invention such as an ELISA are disclosed herein or otherwise known in the art (see, for example, Litt, U.S. Pat. No. 4,092,408, issued May 30, 1978, which is incorporated herein by reference). In particular, a competition ELISA can be useful for diagnosing the presence of a CAEV infection in a sample. A competition ELISA is performed similarly to a standard ELISA, except that one or more monoclonal antibodies, each specific for a CAEV epitope such as the epitopes defined by the CAEV antigens shown in Table 1, is added to the reaction to compete with an anti-CAEV antibody present in the sample. The use of a competition ELISA can produce enhanced sensitivity for detecting the presence of an anti-CAEV antibody in a sample. Methods for performing a competition ELISA such as the threshold ligand receptor assay of Buechler et al. (U.S. Pat. No. 5,089,391, issued Feb. 18, 1992, which is incorporated herein by reference) are well known in the art.

Monoclonal antibodies specific for particular CAEV epitopes can be prepared using well known methods (see, for example, Harlow and Lane, *Antibodies: A laboratory manual* (Cold Spring Harbor Laboratory Press 1988) which is incorporated herein by reference). For example, a mouse can be immunized with a CAEV antigen (see, for example, Table 1), then spleen cells are collected from a mouse having a high titer of antibody for the particular CAEV antigen. Methods for identifying an anti-CAEV antigen antibody having an appropriate specificity and affinity and, therefore, useful in the invention are disclosed herein or otherwise known in the art and include, for example, enzyme-linked immunoadsorption assays, radioimmunoassays and precipitin assays (see Example I; see, also, Harlow and Lane, supra, 1988, chap. 14). The mouse spleen cells can be fused to an appropriate myeloma cell line such as SP/02 or P3x653.Ag8 myeloma cells to produce hybridoma cells. Cloned hybridoma cell lines can be screened using a labelled CAEV antigen to identify clones that secrete monoclonal antibodies specific for the CAEV antigen. Hybridomas that express antibodies having a desirable specificity and affinity can be isolated and utilized as a continuous source of monoclonal antibodies useful in the competition ELISA.

A CAEV antigen can be produced by various methods, including, for example, by recombinant DNA methods or by methods of chemical synthesis. For example, if a CAEV protein or a peptide fragment thereof is desired, the protein or peptide fragment can be produced by cloning the appropriate CAEV coding sequence into an expression vector such as a baculovirus vector and the protein or peptide can be expressed in and isolated from the appropriate host cell. The nucleic acid sequence of CAEV is available as GenBank Accession No. M33677 (see, also, Saltarelli et al., *Virology* 179:347–364 (1990); Knowles et al., *J. Virol.* 65:5744–5750 (1991), each of which is incorporated herein by reference). In addition, it can be desirable to produce the recombinant protein or peptide in a mammalian cell, which can perform a desired post-translational modification. Appropriate expression vectors and host cells are well known in the art and commercially available, and the skilled artisan would know how to select an appropriate vector/host cell system based on a particular need.

Where the CAEV antigen selected is a peptide antigen such as the CAEV antigens exemplified in the Table 1, the peptide can be synthesized using well known method of chemical synthesis, including, for example, automated solid phase methods. Chemical synthesis of a CAEV antigen can be particularly desirable because the method allows for the introduction of amino acid analogs into the peptide. For example, it can be desirable to synthesize a CAEV antigen containing one or a few (D)-amino acid substitutions for corresponding naturally occurring (L)-amino acids. The incorporation of a (D)-amino acid can confer desirable properties on the CAEV antigen, including, for example, increasing the stability of the peptide, which can be particularly useful for preparing a diagnostic kit that is to be distributed to regions of the world where refrigeration is not always available or dependable. In addition, a CAEV peptide can be synthesized and, if desired, can include an additional cysteine residue, which can facilitate specific attachment of the peptide to a solid matrix using appropriate oxidizing conditions.

A method of the invention can diagnose CAEV infection in an individual due, in part, to the presence of anti-CAEV antibodies in a sample obtained from the individual. A sample obtained from an individual suspected of being infected with CAEV is contacted with a CAEV antigen under suitable conditions, which allow the CAEV antigen to bind with an anti-CAEV antibody, if present, in the sample. Thus, a method of the invention can be an ELISA, as exemplified herein, or can be a radioimmunoassay, western blot or other such assay based on the detection of a specific antibody-antigen interaction (see, for example, Harlow and Lane, supra, 1988; see, also, Gribnau et al., U.S. Pat. No. 4,373,932, issued Feb. 15, 1983, which is incorporated herein by reference).

Methods for detecting an antigen-antibody interaction such as the interaction of a CAEV antigen with an anti- CAEV antibody present in a sample are well known in the art and include, for example, the use of a detectably labelled antigen or the use of a detectably labelled second antibody, which is an antibody that specifically binds a particular class of antibody such as IgG, IgA, IgM, IgA, IgD or IgE from a particular mammalian species (see, for example, Greene and David, U.S. Pat. No. 4,376,110, issued August 1983, which is incorporated herein by reference). For example, if a sample is a blood serum or blood plasma sample from a human individual, a second antibody can be a goat, anti-human IgG (see Example I.C.). Such second antibodies can be prepared using well known methods or can be purchased from a commercial source. Methods for detectably labeling a CAEV antigen or an antibody also are well known and routine in the art.

CAEV gp135 was selected as the antigen in the exemplified ELISA because the presence of anti-gp135 antibodies in antiserum collected from a human individual, besides being indicative of infection of the individual with CAEV, also indicates that the individual can have antibodies that are cross-reactive with HIV-1. In fact, 22% of the human individuals identified as CAEV infected by the CAEV ELISA also had antibodies cross-reactive to HIV-1 as determined by HIV-1 ELISA and western blot assays (see Example I.E.). In addition, 55% of the MCTD individuals that were infected with CAEV as determined using the CAEV ELISA also had antibodies cross-reactive to HIV-1.

An ELISA of the invention also can be used to screen mammals other than humans, including, for example, a herd of goats or other mammals susceptible to CAEV infection, to identify CAEV infected individuals. The availability of a simple diagnostic method for identifying CAEV infected goats can be a boon, for example, to the goat farming industry because CAEV infected animals can be identified and removed from the herd well before the clinical signs of CAEV infection occur and before the disease is spread to uninfected goats.

A diagnostic method of the invention is particularly convenient if it is available in the form of a kit. For example, a kit for performing an ELISA can contain a CAEV antigen such as gp135 attached to a solid support such as a plastic support. For example, the kit can contain a microtiter plate such as a 96 well plate containing a CAEV antigen attached to some or all of the wells. Other solid supports useful in an ELISA assay are known in the art. Use, for example, of a 96 well microtiter plate in an ELISA provides the additional advantage that, upon selection of an appropriate detectable label such as a radioactive, fluorescent or luminescent label, the assay can be automated, thereby allowing rapid through put of a large number of samples, including, if desired, appropriate standard or control samples.

A kit such as an ELISA kit also can contain, if desired, a standard reagent such as a predetermined amount of an anti-gp135 antibody. Such reagents can provide a means to readily determine whether a sample such as a blood sample or a blood serum sample obtained from an individual contains an amount of circulating anti-CAEV antibody. Accordingly, a kit of the invention can contain, for example, an appropriate buffer, which provides suitable conditions for binding of an anti-CAEV antibody present in the sample to a CAEV antigen attached to the solid support. In addition, where the ELISA is a competition ELISA, a kit can contain one or more monoclonal antibodies to various CAEV antigens. By providing such reagents in the form of a kit, the ELISA assay can be standardized such that results of different tests performed in different places at different times can be compared with each other. It is recognized that, for a selected CAEV antigen, a population of serum samples obtained from uninfected individuals (controls) should be analyzed in order to determine a base line level of reactivity to the particular CAEV antigen.

A method of the invention such as the exemplified CAEV ELISA can be useful to detect the presence of circulating anti-CAEV antibodies or to follow the development of an immune response. For example, an individual can be vaccinated with a vaccine containing a CAEV antigen and the development of the immune response can be followed using the ELISA. Such a method can be useful for determining whether a booster immunization is required and, if necessary, the optimal time for administering the booster. In addition, a CAEV assay such as the exemplified ELISA can be useful for screening a sample of blood provided by a blood donor in order to identify and remove CAEV contaminated blood from a blood bank.

A peptide fragment of the 70K protein, which is present in the U1 ribonucleoprotein complex, is homologous to an amino acid sequence present in HIV-1 (Douvas and Takehana, *AIDS Res. Hum. Retrovir.* 10:253–262 (1994), which is incorporated herein by reference). As disclosed herein, various peptide fragments of CAEV proteins also are homologous to 70K and HIV-1 sequences and, therefore, can be useful as cross-reacting antigens in a diagnostic method of the invention such as an ELISA, a western blot, or the like. Cross-reacting antigens are useful for the purpose of interpreting cases of false positivity in a diagnostic method of the invention.

Examples of peptide fragments of CAEV that are homologous to amino acid sequences present in 70K and HIV-1 are provided in the Table 1. Other such CAEV peptides useful as a CAEV antigen in a method of the invention can be identified by searching the CAEV DNA or amino acid sequence to identify CAEV peptides that are homologous to the immunologically homologous sequences of 70K and HIV-1 (see Douvas and Takehana, supra, 1994). Furthermore, methods for determining which CAEV peptides that are homologous to 70K and to HIV-1 peptides also are useful as CAEV antigens are disclosed herein, including methods such as an ELISA or a western blot assay (Example I), or otherwise known in the art (see, for example, Harlow and Lane, supra, 1988).

As disclosed herein, exposure of a human individual to CAEV also can stimulate an immune response to CAEV that is cross-reactive with HIV-1 (Example I.E.). CAEV is a retrovirus, subtype lentivirus, that is related to human immunodeficiency virus-1 (HIV-1). CAEV infects goats and causes arthritis and abnormalities of the immune system of infected animals (see, for example, Banks et al., *Arthrit. Rheum.* 30:1046–1053 (1987); Crawford et al., *Science* 207:997–999 (1980)).

Visna maedi virus (VMV) is another lentivirus that is closely related to CAEV and HIV-1 and causes a disease in sheep similar to that caused by CAEV in goats. Thus, VMV or an antigenic fragment of VMV can be substituted for a CAEV antigen or, if desired, can be used in combination with a CAEV antigen in a diagnostic method of the invention.

CAEV causes a persistent infection in goats and is associated with three disease syndromes, including arthritis, which occurs in 20–30% of infected animals; leukoencephalitis, which occurs in young animals; and sporadic neurologic disease, which occurs in adult goats. CAEV infection is found world wide and was identified as the cause of arthritis and encephalitis in goats in 1980. In 1985 and 1986, the relationship between the nucleotide and amino acid sequences of CAEV and HIV-1 (then called HTLV-III) was described. CAEV and HIV-1 are closely related phylogenetically and share a high degree of homology, including, for example, between their RNA dependent DNA polymerases (pol) and between gp120/41 in HIV-1 and gp135/38 in CAEV (see, for example, Gonda et al., *Proc. Natl. Acad. Sci., USA* 83:4007–4111 (1986); Gonda et al., *Retroviridae* 3:83–109 (1994); Garry et al., *Retroviridae* 4:491–603 (1995); each of which is incorporated herein by reference).

CAEV is transmitted among goats through infected milk, particularly colostrum, and infection is spread by the agricultural practice of pooling colostrum to feed young animals. CAEV multiplies in cells of the monocyte/macrophage lineage and in fibroblast cell lines, but does not infect T cells. Macrophages expressing CAEV are distributed in the synovia, lungs, central nervous system, lymph nodes, spleen, gastro-intestinal tract and mammary glands of infected goats.

Prior to the present disclosure, CAEV was not known to infect humans. However, the detection of seroconversion by ELISA and western blot analyses using human blood samples (Example I.C.) and the detection of proviral DNA, corresponding to CAEV gag and pol genes, by polymerase chain reaction (PCR) analysis in genomic DNA obtained from an MCTD patient (Example I.D.) provides demonstrative evidence that CAEV infects humans. The incorporation of viral DNA sequences into host cell DNA is a hallmark of infection by the lentiviruses, including CAEV and HIV-1.

Based on the results disclosed herein, CAEV may infect as many as half the population of Mexico and Central America, particularly those who consume raw goat milk, which is common in these areas, or are otherwise exposed to goats (see Example I.C.). Although there is no evidence that CAEV causes a pathologic condition in humans, it is important, nevertheless, to determine the scope of CAEV infection in the human population in order to identify whether, for example, a pathology of unknown etiology correlates with CAEV infection. The ELISA assay provided herein allows for routine screening for CAEV infection in humans and provides the additional advantage of being useful for screening goats or other mammals to identify the presence of CAEV infection.

PCR analysis also was performed on genomic DNA obtained from three groups of goats from different geographical regions and from a CAEV infected human (see Example I.D.). The PCR analysis of human and goat genomic DNA identified at least two potential strains of CAEV, which differ from the DNA sequence of a reference CAEV strain (reference CAEV DNA sequence is available as GenBank Accession No. M33677, which is incorporated herein by reference). Remarkably, the immune responses generated in two of the three groups of CAEV infected goats and in several CAEV infected human individuals were cross-reactive with HIV-1.

CAEV infected goats have been used as an animal model for human rheumatoid arthritis, which is the most well known and prevalent syndrome in a cluster of arthritic/autoimmune disorders, the systemic rheumatic disorders. The systemic rheumatic disorders are about three times more common in women than men.

Mixed connective tissue disease (MCTD) is another systemic rheumatic disorder. MCTD is characterized by autoantibodies to the U1 snRNP splicing complex. MCTD is considered to be an overlap syndrome, in that it embraces clinical and serologic features common to three other systemic rheumatic disorders—systemic lupus erythematosus (SLE), scleroderma and polymyositis. The clinical profile of MCTD includes arthritis, lymphadenopathy, vasculitis, myositis, Sjogren's syndrome (lymphocytic infiltration of salivary and lacrimal glands) and immune dysregulation.

The clinical profile manifest in MCTD individuals also occurs in HIV-1 infected individuals. However, these clinical manifestations have a more severe course and are more refractory to therapy in HIV-1 infected persons. For example, Sjogren's syndrome in MCTD individuals is characterized by localized lymphocytic infiltration, whereas widespread glandular infiltration, referred to as diffuse infiltrative lymphocytosis syndrome, occurs in the corresponding HIV-1 associated syndrome.

Severe necrotizing vasculitis accompanied by neuropathy, inflammatory polymyopathy unrelated to drug therapy and other forms of vascular and neuromuscular disease associated with rheumatic disorders also occur in HIV-1 infected individuals. Necrotizing lymphadenopathy, which results in massive destruction of lymph node structure, occurs in MCTD, SLE and HIV-1 infection. Two classical rheumatic disorders, psoriatic arthritis and Reiter's syndrome, are the earliest manifestations of HIV-1 infection and are more refractory to chemotherapeutic agents when associated with HIV-1 infection.

The clinical similarities of HIV-1 infection in humans, CAEV infection in goats and the systemic rheumatic disorders such as MCTD suggest that HIV-1 can be a precipitant of rheumatic pathology or that a phylogenetically related, but more clinically benign lentivirus such as CAEV is an etiologic factor in rheumatic disorders. Serologically, MCTD is characterized by the presence of anti-ribonucleoprotein (RNP) antibodies specific for the U1 snRNP particle, which is positioned at 5'-end of introns during nuclear RNA splicing. Anti-RNP antibodies also are present in some SLE and scleroderma patients. The U1 snRNP particle is composed of a core of U1 RNA and a cluster of RNA binding proteins, including the 70K, A and C proteins. Anti-RNP antibodies inhibit RNA splicing by binding U1 snRNP.

Although the humoral anti-RNP autoantibody response is pathognomonic in MCTD, the 70K protein, for example, contains both T cell and B cell epitopes and the humoral and cellular autoimmune manifestations are interdependent. T cell clones responsive to 70K epitopes have been isolated and include $CD8^+$ T cells having cytotoxic T lymphocyte activity and $CD4^+$ T cells having helper T cell activity. Some of the 70K T cell epitopes are homologous to T cell epitopes of HIV-1 (see Douvas and Takehana, supra, 1994). As disclosed herein, CAEV proteins, including CAEV gp135, also contain epitopes that are homologous to 70K and HIV-1 T cell epitopes (see Table 1, supra).

In view of the clinical similarities of HIV-1 infection and MCTD and the identification of CAEV infection in MCTD patients and in otherwise healthy individuals, it was important to determine whether individuals infected with CAEV develop an immune response that cross-reacts with HIV-1. The level of immunity to the HIV-1 protein, gp120, in blood obtained from CAEV infected individuals was examined by ELISA and by western blot analysis (see Example I.E.). In addition to exploring the relationship between CAEV infection and the development of an immune response to HIV-1, the relationship between CAEV infection and MCTD was investigated. Since some MCTD patients from Mexico or Central America have antibodies that react to HIV-1 gp120 and inhibit HIV-1 infectivity in vitro, it remained to be established whether CAEV infected persons that do not have MCTD also develop immunity to HIV-1.

As disclosed herein, CAEV infection in humans, whether suffering from MCTD or otherwise healthy, stimulated a humoral immune response that cross-reacted with the HIV-1 gp120 or p24 viral antigen (see Example I.E.). Significantly, none of the humans examined was infected by HIV-1 as determined using clinically certified assays. These results indicate that immunization of an individual with a CAEV antigen can generate cross-reactive immunity to HIV-1, thereby increasing the resistance to HIV-1 infection in an uninfected individual or reducing the severity of a pathology due to HIV-1 in an HIV-1 infected individual. Furthermore, the presence of a systemic rheumatic disorder such as MCTD in a CAEV infected patient substantially increased the level of HIV-1 cross-reactivity (Example I.E.).

The following examples are intended to illustrate but not limit the present invention.

EXAMPLE I

CHARACTERIZATION OF HIV-1 CROSS-REACTIVITY IN CAEV INFECTED INDIVIDUALS

This example describes the methods used to demonstrate that CAEV infected individuals generate an immune response that is cross-reactive with HIV-1 gp120.

A. Human Subjects:

More than 50 human subjects were involved in the studies disclosed herein. The subjects were categorized based on their disease status (MCTD or normal) and their place of origin (Mexico/Central America or the United States) and were grouped as follows:

Group A. MCTD—Hispanic born females, clinically diagnosed with MCTD.

Group B. MCTD—U.S. born black or Caucasian females, clinically diagnosed with MCTD.

Group C. MCTD—Guadalajara female residents, clinically diagnosed with MCTD.

Group D. Normal (non-MCTD)—Hispanic born females.

Group E. Normal—non-Hispanic males and females, including two workers in a veterinary service that treats infected goats.

Group F. Normal—4 female and 4 male residents of a village located 30 km from Guadalajara, including the owner of a herd of 150 goats and 5 members of his family.

Group G. Scleroderma patients, all having anti-Scl-70/type 1 antibodies.

B. Blood Samples and Reagents:

Human and goat (see Section I.F., below) blood samples were collected and the serum component was used for immunologic testing. The antigens used in the ELISA and western blot assays to measure levels of serum antibodies included crude CAEV and affinity purified gp135 and recombinant HIV-1 gp120 and HIV-1 p24. Recombinant HIV-1 gp120 and p24 were purchased from Intracel (Shepreth UK).

Crude CAEV is prepared as described by Klevjer-Anderson et al., (*Virology* 110:113–119 (1981), which is incorporated herein by reference). Essentially, CAEV is grown in primary fetal goat synovial membrane (SM) cells grown in DMEM with a bicarbonate-HEPES buffer supplemented with 2 mM glutamine, 100 mg/ml streptomycin and 100 units/ml penicillin and containing 10% FBS. Medium of CAEV infected SM cultures is collected and clarified by centrifugation at 600×g.

Aliquots of the crude CAEV preparation can be stored frozen at −70° C. The crude CAEV preparation can be used to isolate purified CAEV or can be used to prepare purified CAEV proteins. Purified CAEV proteins such as purified CAEV gp135 also can be prepared by cloning a nucleic acid molecule encoding gp135 (GenBank Accession NO. M33677; see, also, Saltarelli et al., supra, 1990; Knowles et al., supra, 1991) into an expression vector using routine methods of recombinant DNA technology and purifying the gp135 as described below.

CAEV gp135 is affinity purified from the crude CAEV preparation using an anti-gp135 antibody conjugated to a chromatography matrix. Essentially, the crude CAEV preparation is adjusted to 0.1% SDS to lyse the CAEV viral particles, then applied to an anti-gp135 antibody affinity chromatography column or recombinantly produced gp135 is applied to the affinity column.

Anti-gp135 antibody is isolated from CAEV infected goat serum or from serum obtained from goats immunized with a peptide fragment of CAEV gp135. If a CAEV infected goat is used as the source of serum, a goat having a high titer of anti-gp135 antibodies is used as the source of serum. Such serum can be identified by using western blot analysis to screen serum samples obtained from several different goats. Anti-gp135 antibodies are isolated from the serum by ammonium sulfate precipitation, followed by column chromatography to obtain the IgG fraction. The anti-gp135 antibodies are attached to a chromatography matrix such as cyanogen bromide activated Sepharose™. Methods for isolating IgG antibodies and attaching such antibodies to a matrix are well known and routine in the art (see, for example, Harlow and Lane, supra, 1988).

The crude CAEV preparation or recombinantly produced gp135 in PBS is loaded onto the anti-gp135 antibody affinity column and gp135 is allowed to bind to the antibodies overnight at 4° C. Following binding, the column is washed with PBS, then bound gp135 is eluted with 10 mM HCl, 0.15 M NaCl. Purity of the gp135 antigen is determined by SDS-PAGE and silver staining.

C. CAEV ELISA and Western Blot Assays:

For ELISA assays, crude CAEV or affinity purified gp135 antigen was diluted 1:20 with phosphate buffered saline (PBS; final concentration gp135 approx. 1 µg/ml) and 50 µl was added to each well of a 96 well plate (Corning). The plate was covered and incubated overnight at 4° C., then antigen was removed and the wells were washed 3× for 1 min each with 90 µl washing solution (1 mg BSA/ml PBS). 100 µl blocking solution (10 mg BSA/ml PBS) was added to each well and plates were incubated 60 min at room temperature (RT), then the blocking solution was removed and the wells were washed 3× for 1 min each with washing solution.

Fifty µl of diluted serum sample (1:100 in washing solution) was added to each well and plates were incubated 60 min at RT. Blank (control) wells contained washing solution, alone. Following incubation, wells were washed as above, then 50 µl diluted second antibody was added and incubated as above. Where the serum sample to be analyzed was from humans, the second antibody was goat anti-human IgG conjugated to horse radish peroxidase (HRP; Zymed Laboratories, Inc.; South San Francisco Calif.; cat. # 62-8420) diluted 1:1000 in PBS. Where the serum sample to be analyzed was from goats, the second antibody was rabbit anti-goat IgG-HRP (Jackson ImmunoResearch Labs, Inc.; West Grove Pa.; cat. # 305035003, lot # 28671) diluted 1:3000 in PBS. Following incubation, wells were washed 2× with washing solution, then 2× with PBS.

Seventy-five µl color development solution (10 mg O-phenyldiamine (Sigma) in 25 ml ELISA buffer; 50 µl 30% $H_2O_2$, prepared fresh; ELISA buffer is 500 ml 0.1M citric acid, 500 ml 0.2M $Na_2HPO_4$, adjusted to pH 5.0) was added to each well and incubated 10 min at RT in the dark. Color development was terminated by adding 25 µl 6N $H_2SO_4$, then absorption was measured at $OD_{490}$.

For CAEV western blot analysis, 0.1–0.5 µg aliquots of gp135 in SDS sample buffer (Laemmli, *Nature* 227:680–685 (1970), which is incorporated herein by reference), were separated by 10% SDS-PAGE, then transferred electrophoretically onto a nitrocellulose membrane. The membrane was incubated for 1 hr in 50 ml blocking buffer (1% BSA in WBS; WBS is 9 g NaCl, 1.21 g Tris-base, 0.25 ml NP-40 made up to 1 liter, pH 7.4), then washed 3× with washing buffer (0.1% BSA in WBS). The membrane was cut into strips, representing the lanes on the gel.

Serum samples were diluted 1:100 (20 µl serum/2 ml washing buffer; 40 µl/2 ml if plasma used), then added to an incubation tray containing a nitrocellulose strip and shaken for 60 min at RT. Following incubation, the strips were washed 3× with washing buffer, then 2 ml second antibody (as above, but diluted with washing buffer) was added and incubation continued for 60 min at RT. Strips were washed 3× with washing buffer and the enzyme reaction was initiated by adding 2 ml color development solution (10 mg 3,3-diaminobenzidine tetrahydrochloride (Sigma Chemical Co.; St. Louis Mo.; cat. # D 5905), 1 ml 0.05M Tris, pH 7.5, 39 ml WBS, 80 µl $H_2O_2$, prepared fresh). Incubation was continued from 10 min at RT with gentle shaking, then color development was terminated by transferring the membrane to distilled water.

High reactivity to extracts of CAEV and to purified gp135 was observed in 62% of the serum samples obtained from Hispanic born MCTD patients (Table 2),

TABLE 2

The relationship between CAEV gp135 and HIV-1 gp120 reactivity in MCTD patients and normals

| postitive gp135 | | negative gp135 | |
|---|---|---|---|
| 1. MCTD n = 22; hispanic = 20 | | 3. MCTD n = 17; hispanic = 13 | |
| total gp120(+) $\frac{12}{22}$ = 55% | | total gp120(+) $\frac{0}{17}$ = 0% | |
| hispanic gp120(+) $\frac{11}{20}$ = 55% | | hispanic gp120(+) $\frac{0}{13}$ = 0% | |
| 2. NL n = 11; hispanic = 9 | | 4. NL n = 9; hispanic = 5 | |
| total gp120(+) $\frac{4}{11}$ = 36% | | total gp120(+) $\frac{0}{9}$ = 0% | |
| hispanic gp120(+) $\frac{2}{9}$ = 22% | | hispanic gp120(+) $\frac{0}{5}$ = 0% | |
| Summary 1: | CAEV(+) | | |
| | Total Hispanic | 29/47 = 62% | |
| | MCTD - hispanic | 20/33 = 61% | |
| | NL - hispanic | 9/14 = 64% | |
| | Total Nonhispanic | 2/15 = 13% | |
| | MCTD - nonhispanic | 2/6 = 33% | |
| | NL - nonhispanic | 2/6 = 33% | |
| Summay 2: | CAEV(+)/gp120(+) | | |
| | hispanic MCTD | 12/22 = 55% | |
| | hispanic NL | 2/9 = 22% | |
| | CAEV(−)/gp120(+) | | |
| | hispanic MCTD and NL | 0/20 = 0% | |
| | non-hispanic MCTD and NL | 0/11 = 0% | | including those from LAC/USC (group A) and those from Guadalajara, Mexico (group C). Serum samples from the disease control (group G) and from non-Hispanic healthy individuals, excluding the two veterinarians, were weakly reactive or non-reactive. The human serum samples that reacted to CAEV on western blots contained antibodies to the same polypeptides as those reacting with serum samples obtained from CAEV infected goats.

The reactivity to CAEV of serum samples from the normal individuals correlated with a history of drinking raw goat milk or other exposure to goats. The highest reactivities were present in the owner of the Guadalajara goat herd and in one of the veterinarians, who, in addition to treating CAEV infected goats, also reported regularly consuming raw goat milk. The second veterinarian, who also treated CAEV infected goats, also had positive reactivity.

In summary, 22 of 39 MCTD patients and 11 of 23 non-MCTD individuals had positive reactivity for CAEV infection, including 20 of 33 Hispanic MCTD patients (61%) and 9 of 14 Hispanic non-MCTD individuals (64%; see Table 2). These results indicate that over 60% of the Hispanic individuals examined in this study were infected with CAEV. In the CAEV reactive individuals, the reactivity of serum obtained from Hispanic MCTD patients was higher than that of the non-MCTD Hispanic individuals.

D. PCR Analysis:

PCR analysis for identification of CAEV gag and pol genes was performed using genomic DNA isolated from peripheral blood mononuclear cells (PBMC). PBMC were obtained by Ficoll density gradient centrifugation of whole citrated or heparinized blood collected from selected human individuals and from WA, UC Davis and Gua goats (see below).

CAEV-specific genomic DNA sequences encoding regions of the gag protein were amplified in two stages. The first stage produced amplification products representing nucleotides 1057 to 1553 of CAEV. Primers were 5'-GCAGTTGGCATATTATGCTACTAC-3' (SEQ ID NO: 14; CAEV nucleotides 1057–1080) and 5'-CTTGTTGTACTCTTTGTCCTAGTG-3' (SEQ ID NO: 15; nucleotides 1530–1553). The second stage produced amplification products within the product of the first amplification product, from nucleotides 1329 to 1501. The primers for the second stage were 5'-GAGCAGTAAGACATATGGCGGCAC-3' (SEQ ID NO: 16; nucleotides 1329–1351) and 5'-TGATGCATTTGTATATAAGATAGTGTTAGCTT-3' (SEQ ID NO: 17; nucleotides 1471–1510).

DNA encoding the CAEV pol also was examined by PCR analysis. Primers for the first stage of amplification were 5'-GGATTTGAACTACACCCGCAG-3' (SEQ ID NO: 18; CAEV nucleotides 2845–2865) and 5'-CCTGTTGATACTATGAACCCTAGAC-3' (SEQ ID NO: 19; nucleotides 3404–3518); primers for the second stage were 5'-AAGAACCTAAGCATCCCGCAAC-3' (SEQ ID NO: 20; nucleotides 3223–3244) and 5'-GTGATGTTCCCTAATTGCAATTCTAGTC-3' (SEQ ID NO: 21; nucleotides 3341–3368).

Amplifications were performed using an annealing temperature of 52° C. and an elongation temperature of 72° C. and were allowed to proceed for 38 cycles. Taq polymerase or pfu Taq polymerase (Promega Corp.; Madison Wis.) was used as recommended by manufacturer. One µl of the reaction mixture from the first stage of amplification was used for the second stage of amplification, which was performed under identical conditions. The products following the second stage of amplification were separated by agarose electrophoresis and collected by eluting the appropriate band. The amplified DNA samples then were cloned into a TA3 pCR™ vector (Invitrogen; La Jolla Calif.) and sequenced using a Sequenase™ Version 2.0 DNA sequencing kit (U.S. Biochemical Corp.; Cleveland Ohio) as recommended by the manufacturer. The cloned DNA sequences were compared to a reference CAEV DNA sequence (GenBank Accession No. M33677).

PCR analysis revealed that CAEV proviral DNA was present in genomic DNA of individuals that were CAEV positive as determined by ELISA or western blot analysis. Specifically, DNA encoding CAEV gag and pol sequences was amplified from genomic DNA of an MCTD patient (group A) and from the CAEV infected UC Davis goat. Comparison with the reference CAEV gag sequence demonstrated that the gag sequence in the MCTD patient diverged from the reference sequence by 8.2% and that the gag sequence in the UC Davis goat diverged by 8.8%. In addition, comparison with the reference CAEV pol sequence demonstrated that the CAEV pol sequence in the MCTD patient diverged by 7.6% and the CAEV pol sequence in the UC Davis goat diverged by 7.6%.

The relatively high degree of similarity between the CAEV sequences present in the human genomic DNA samples and the reference goat CAEV sequence provides definitive evidence of CAEV infection in humans. The average divergence of about 8% between the sequences indicates that the human CAEV infection can be due to a distinctive, human-adapted CAEV strain. Additional DNA sequencing can clarify whether a human-adapted CAEV strain is responsible for human CAEV infection.

E. HIV-1 ELISA and Western Blot Assays:

Certified HIV-1 ELISA and western blot diagnostic kits were purchased from Organon Teknika (Cambridge UK) and the assays were performed as recommended by the supplier. Based on the clinical criteria using the certified HIV-1 ELISA and western blot assays, all of the human serum samples were negative for HIV-1, except for known HIV-1 positive sera and antibodies used as positive controls.

ELISA and western blot assays were performed using the individual recombinant HIV-1 antigens, gp120 and p24, and HRP-conjugated rabbit anti-goat and goat anti-human second antibodies (Zymed Laboratories Inc.) as previously described (Douvas and Takehana, supra, 1994; Crow et al., *Cell. Immunol.* 121:99–112 (1989), which is incorporated herein by reference). Subsets of sera that reacted with CAEV gp135 also reacted with HIV-1 gp120, including a total of 12 MCTD sera reacted with HIV-1 gp120 (see Table 2, supra).

As discussed in Section I.C., above, 22 of 39 MCTD patients and 11 of 23 non-MCTD individuals were positive for CAEV infection, including 20 of 33 Hispanic MCTD patients (61%) and 9 of 14 Hispanic non-MCTD individuals (64%; Table 2). The results of the HIV-1 assays further indicated that 12 of the 22 CAEV positive Hispanic MCTD patients (55%) and 2 of the 9 CAEV positive Hispanic non-MCTD individuals (22%) also showed positive reactivity to HIV-1 gp120 (see Table 2). In contrast, none of the CAEV negative Hispanic MCTD or non-MCTD individuals was positive for HIV-1 gp120.

These results indicate that CAEV infection of otherwise healthy individuals occurs without the concomitant development of clinical disease, including without developing symptoms of MCTD. However, exposure to CAEV results in the development of an immune response to CAEV that generalizes to HIV-1 in a subset of infected individuals. In addition, in CAEV positive MCTD patients, the reactivity to CAEV is about 1.6 times stronger than in CAEV positive non-MCTD individuals and the frequency of cross-reactivity to HIV-1 gp120 is more frequent. These results demonstrate that cross-reactivity to HIV-1 develops as a result of infection with CAEV and that the cross-reactive immune response is increased in an individual with an autoimmune disease.

F. CAEV Infected Goats:

Three groups of goats were studied as follows:

Group I. WA—uninfected goats and experimentally infected (CAEV) goats maintained at Washington State University, Pullman Wash.

Group II. UC Davis—a naturally infected (CAEV) goat maintained at the University of California, Davis Calif.

Group III. Gua—20 naturally infected (CAEV) goats belonging to a goat herder in Guadalajara Mexico (see Group F. above).

Serum samples collected from the various CAEV infected or uninfected goats were examined. The Gua goats (Group III) lacked reactivity to CAEV gp135 but about 50% were reactive against CAEV gp38 and gag. In addition, the Gua goats, but not the WA goats showed strong reactivity to HIV-1 gp120 and p24. The UC Davis goat was reactive against both gp135, gp120 and p24.

These results demonstrate that differences exist between the immunologic reactivities of the WA and Gua goats to CAEV and to HIV-1 antigens. These differences may derive from different viral strains or may be due to the different routes of infection. For example, the WA goats were infected intravenously, whereas the Gua goats and the UC Davis goat were naturally infected via ingestion of infected milk.

Although the invention has been described with reference to the examples above, it should be understood that various modifications can be made without departing from the spirit of the invention. Accordingly, the invention is limited only by the following claims.

We claim:

1. An immunolgic method of diagnosing a CAEV infection in a human suspected of being infected with CAEV, comprising the steps of:
  a. obtaining a human sample;
  b. contacting said human sample with a CAEV antigen under suitable conditions; and
  c. detecting specific binding of an anti-CAEV antibody present in said sample to said CAEV antigen, wherein the detection of said specific binding is diagnostic of the human being infected with CAEV infection.

2. The method of claim 1, wherein said human sample obtained is a serum sample.

3. The method of claim 1, wherein said CAEV antigen is attached to a solid support.

4. The method of claim 3, wherein said detecting step is accomplished by ELISA.

5. The method of claim 4, wherein said ELISA is a competition ELISA.

6. The method of claim 1, wherein said CAEV antigen is CAEV gp135.

* * * * *

UNITED STATES PATENT AND TRADEMARK OFFICE
CERTIFICATE OF CORRECTION

PATENT NO : 5,770,357
DATED : June 23, 1998
INVENTOR(S): Angeline Douvas, Glenn Ehresmann It is certified that error appears in the above-identified patent and that said Letters Patent is hereby corrected as shown below:

On title page, After paragraph [76] Inventors:

Add the following paragraph:

Assignee: Southern California, University of
 University Park
 Los Angeles, California Signed and Sealed this Fourth Day of July, 2000

Attest:

Q. TODD DICKINSON

Attesting Officer

Director of Patents and Trademarks